(12) United States Patent (10) Patent No.: US 6,893,259 B1
Reizenson (45) Date of Patent: May 17, 2005

(54) ORAL HYGIENE DEVICE AND METHOD OF USE THEREFOR

(76) Inventor: Igor Reizenson, 212 Creekway Crossing, Smyrna, GA (US) 30082

( * ) Notice: Subject to any disclaimer, the term of this patent is extended or adjusted under 35 U.S.C. 154(b) by 14 days.

(21) Appl. No.: 10/795,816

(22) Filed: Mar. 8, 2004

(51) Int. Cl.⁷ .............................. A61C 1/00; A61C 5/02
(52) U.S. Cl. ........................................ 433/29; 433/80
(58) Field of Search ............................ 433/29, 80, 215, 433/216; 601/164

(56) References Cited

U.S. PATENT DOCUMENTS

| | | | |
|---|---|---|---|
| 2,957,476 A | 10/1960 | Freeman | |
| 3,527,218 A * | 9/1970 | Westine | ................. 433/80 |
| 3,566,869 A | 3/1971 | Crowson | |
| 3,669,101 A | 6/1972 | Kleiner | |
| 3,731,675 A | 5/1973 | Kelly | |
| 3,742,942 A | 7/1973 | Westline | |
| 4,059,101 A | 11/1977 | Richmond | |
| 4,106,501 A * | 8/1978 | Ozbey et al. | ............. 601/164 |
| 4,164,940 A | 8/1979 | Quinby | |
| 4,192,071 A | 3/1980 | Erickson | |
| 5,104,315 A | 4/1992 | McKinley | |
| 5,365,624 A | 11/1994 | Berns | |
| 5,487,662 A * | 1/1996 | Kipke et al. | ............. 433/37 |
| 6,077,073 A * | 6/2000 | Jacob | ............. 433/29 |
| 6,152,733 A | 11/2000 | Hegemann et al. | |
| 6,162,055 A | 12/2000 | Montgomery et al. | |
| 6,391,283 B1 | 5/2002 | Jensen et al. | |
| 6,439,889 B1 | 8/2002 | Chen et al. | |
| 2002/0137001 A1 * | 9/2002 | Cipolla et al. | ............. 433/29 |
| 2003/0104341 A1 | 6/2003 | Zavitsanos et al. | |

* cited by examiner

*Primary Examiner*—Cary E. O'Connor
(74) *Attorney, Agent, or Firm*—Myers & Kaplan, LLC; Ashish D. Patel

(57) ABSTRACT

An oral hygiene device including, in combination, a system for relatively effortlessly and effectively cleansing dental, inter-dental, gingival and deep-gum surfaces and crevices, and a convenient teeth bleaching system that may be selectively implemented following cleansing of the oral surfaces, wherein the present invention may be utilized in conjunction with, or in lieu of, conventional brushing and/or flossing practices.

26 Claims, 5 Drawing Sheets

ORAL HYGIENE DEVICE AND METHOD OF USE THEREFOR

TECHNICAL FIELD

The present invention relates generally to dental care apparatuses, and more specifically to an oral hygiene device suitable for in-home use and adapted to provide a user with effective dental and gingival cleansing, inter-dental and deep-gum bacterial plaque removal, and a conveniently incorporated teeth whitening or bleaching system.

BACKGROUND OF THE INVENTION

In addition to regular professional dental checkups, daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental bacterial plaque, tarter and/or food particulate. As such, most individuals resort to biannual professional dental cleanings to remove such residual or vestigial bacteria, tarter deposits, and the like.

Children are also encouraged, either through in-school programs or at-home parental enforcement and supervision, to care for their newly developing teeth. Accordingly, children are often guided to brush their teeth each morning and after every meal, and to both floss and brush before bedtime. However, as most parents will likely concur, training children to commit or adhere to such regular dental care is tasking and difficult, if not impossible, and is often short-lived. In large part, many children would likely agree that brushing is a relatively mundane task, done only to obey parental instruction. Still other children would argue that flossing is much too painful or arduous a task to practice daily—indeed, many adults would be of similar opinion. Therefore, it would appear that conventional methods of daily or regular oral hygiene inflict an almost painfully obligatory task upon an individual, as opposed to a voluntary task readily and freely undertaken in an attempt to maintain a healthy mouth.

Additionally, although regular oral hygiene ensures healthy gums and teeth, the surface of each tooth is not immune from eventual discoloration or staining from foods or liquids, such as food dyes, teas and coffees, or chemical stains, such as those from medications, cigarettes and other tobacco products. Accordingly, many individuals often resort to bleaching processes to enhance the surface aesthetics or whiteness of their teeth, wherein many such bleaching processes are offered through professional dental practices, and/or via the purchase of at-home bleaching kits.

Typical bleaching systems offer bleaching or whitening gels that are applied over each tooth surface or to mouth trays adapted to fit over each row of teeth, wherein such bleaching gels comprise hydrogen peroxide or other chemicals as the active bleaching agent. Additionally, some clinical professionals have found that the effectiveness of some chemical bleaching compounds is enhanced via the application of a suitable light source over the tooth surface following application of the bleaching compound thereover. Unfortunately, such light-activated bleaching processes are often only offered through professional dental practices or clinics, and impart significant cost unto the patient electing such a procedure. Furthermore, following such bleaching procedures, many individuals often continue to indulge or partake in the same dietary habits or tobacco-based usage habits causative of the original stains or discoloration. Unfortunately, no effective and practical re-cleaning and re-bleaching system is available for daily consumer use to offset the counter-whitening effects of such stain-inducing products.

Therefore, it is readily apparent that there is a need for an oral hygiene device including, in combination, a system for relatively effortlessly and effectively cleansing dental, inter-dental, gingival and deep-gum surfaces and crevices, and a convenient teeth bleaching system that may be selectively implemented following cleansing of the oral surfaces, wherein the present invention may be utilized in conjunction with, or in lieu of, conventional brushing and/or flossing practices. There is a further need for such a device that may be utilized by those individuals suffering from physical incapacities that may hinder the practice of regular oral hygiene, wherein such individuals may include the elderly, arthritis sufferers, paraplegics, quadriplegics, bed-ridden individuals, hospitalized individuals, and the like.

BRIEF SUMMARY OF THE INVENTION

Briefly described, in a preferred embodiment, the present invention overcomes the above-mentioned disadvantages and meets the recognized need for such a device by providing an in-home, automated oral hygiene device incorporating a dual-purpose oral hygiene system adapted to be in utilized in association with, or in place of, conventional brushing, flossing and/or bleaching practices, wherein an individual may selectively elect a full oral cleansing followed by a teeth bleaching process, if desired.

According to its major aspects and broadly stated, the present invention in its preferred form is an oral hygiene device and method of use therefor, comprising, in general, a mouth tray, dispersion tube, collection tube, light source and associated light carriers, and pump unit.

More specifically, the present invention is an oral hygiene device and method of use therefor, comprising a mouth tray adapted to fit over a user's teeth and gums, wherein the mouth tray comprises a plurality of throughholes, orifices or ports. Preferably extending from the mouth tray is a dispersion tube and a collection tube, wherein the dispersion tube and collection tube are preferably in fluid communication with a pump unit.

The pump unit is preferably adapted to retain, pump and convey dental cleaning solution through the dispersion tube for subsequent dispersion of same through the plurality of orifices of the mouth tray, and thereafter, over the user's teeth and gums, thereby cleansing same. That is, the pump unit preferably pumps cleaning solution through the mouth tray with sufficient force and in a pulsating manner so as to effectively loosen and/or dislodge surface, deep-gum and/or deep inter-dental bacterial plaque, tarter and/or food particulate.

Thereafter, the pump unit suctions the dispersed cleaning solution from the user's mouth and mouth tray via the collection tube, wherein the cleaning solution, along with the removed bacterial plaque, tarter and/or food particulate, is preferably drawn through the collection tube and channeled into a collection reservoir contained within the pump unit. If desired, the pump unit may contemporaneously disperse cleaning solution and suction same, thus maintaining a fresh supply of dental cleaning solution within the user's mouth at all times. The dispersion reservoir (i.e., reservoir containing the dental cleaning solution) and/or collection reservoir of the pump unit may each be removed from the pump unit and rinsed or disinfected accordingly. Alternatively, it is contemplated that the dispersion reservoir, and in particular, the collection reservoir, could each comprise a manual or automated drainage or plumbing system to enable the flushing of cleaning solution and/or dirty cleaning solution, respectively, therefrom, wherein suitable sanitizing solutions or disinfectants may be subsequently introduced therein and, thereafter, flushed or drained therefrom, thereby supporting a larger clinical application of the present invention.

Preferably, side-emitting fiber optic light lines, or other suitable light carriers, emitters and/or sources (i.e., side-emitting fiber optic light lines, lasers, blue light, light-emitting diodes, flat woven fiber optic panels or strips, and/or the like), are disposed along the exterior side or frontal surface of the mouth tray. As such, a light-activated bleaching compound may be applied directly to the teeth, the teeth reservoirs of the mouth tray, or delivered via the pump unit over the teeth, wherein the conveyance of light through the fiber optic light lines preferably illuminates, and thus activates, the bleaching compound over the teeth to enable the bleaching or whitening thereof. It is further contemplated that the fiber optic light lines may be illuminated during the cleansing process of the teeth, wherein a suitable bleaching compound could be intermixed with, or applied in conjunction with, the dental cleansing solution over the teeth and gums, for activation via the fiber optic light source.

Accordingly, a feature and advantage of the present invention is its ability to provide an automated oral hygiene device incorporating, in combination, a teeth and gum cleansing system, and a teeth bleaching system.

Another feature and advantage of the present invention is its ability to be in utilized in conjunction with, or in lieu of, conventional brushing, flossing and/or bleaching practices.

Still another feature and advantage of the present invention is its ability to effectively loosen and/or dislodge surface, deep-gum and/or deep inter-dental bacterial plaque, tarter and/or food particulate.

Yet another feature and advantage of the present invention is its incorporation of a light source and light carriers for activating light/photon-activated bleaching compounds.

Yet still another feature and advantage of the present invention is its ease of use.

A further feature and advantage of the present invention is its suitability for in-home application, thereby facilitating the implementation of regular and dedicated oral hygiene regimens for children and adults alike.

Still a further feature and advantage of the present invention is its incorporation of removable dispersion and collection reservoirs.

Still yet a further feature and advantage of the present invention is its ability to replace expensive professional dental bleaching processes.

Still yet another and further feature and advantage of the present invention is its ability to be utilized by those individuals suffering from physical incapacities that may hinder the practice of regular oral hygiene, wherein such individuals may include the elderly, arthritis sufferers, paraplegics, quadriplegics, bed-ridden individuals, hospitalized individuals, and the like.

Yet another feature and advantage of the present invention is its ability to be utilized in the provision of care to patients within professional dental clinics.

These and other features and advantages of the present invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Alternate Embodiments with reference to the accompanying drawing figures, in which like reference numerals denote similar structure and refer to like elements throughout, and in which.

DETAILED DESCRIPTION OF THE PREFERRED AND SELECTED ALTERNATIVE EMBODIMENTS

Figure 1:
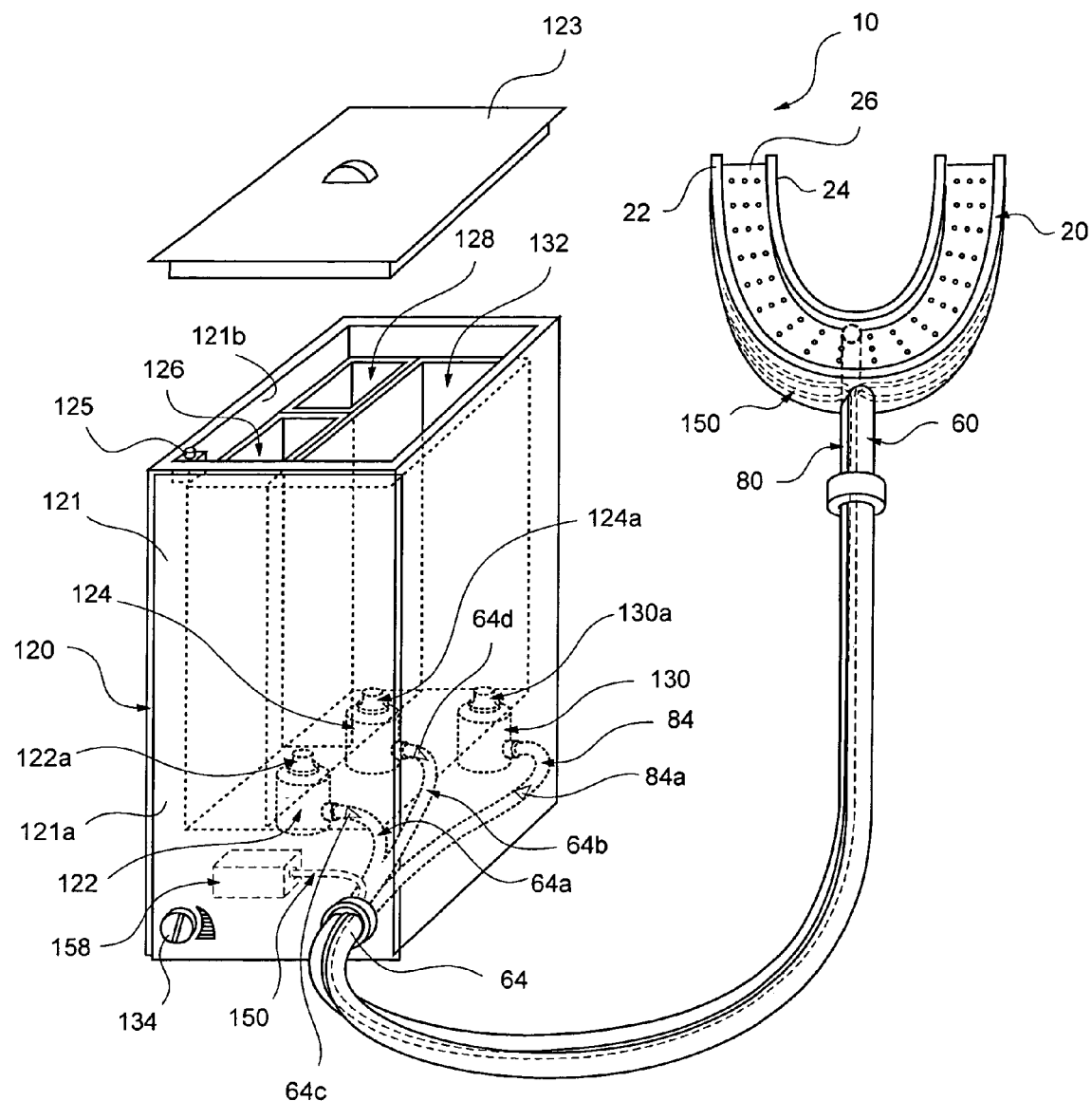
FIG. 1 is a perspective view of an oral hygiene device according to a preferred embodiment of the present invention.
Figure 2:
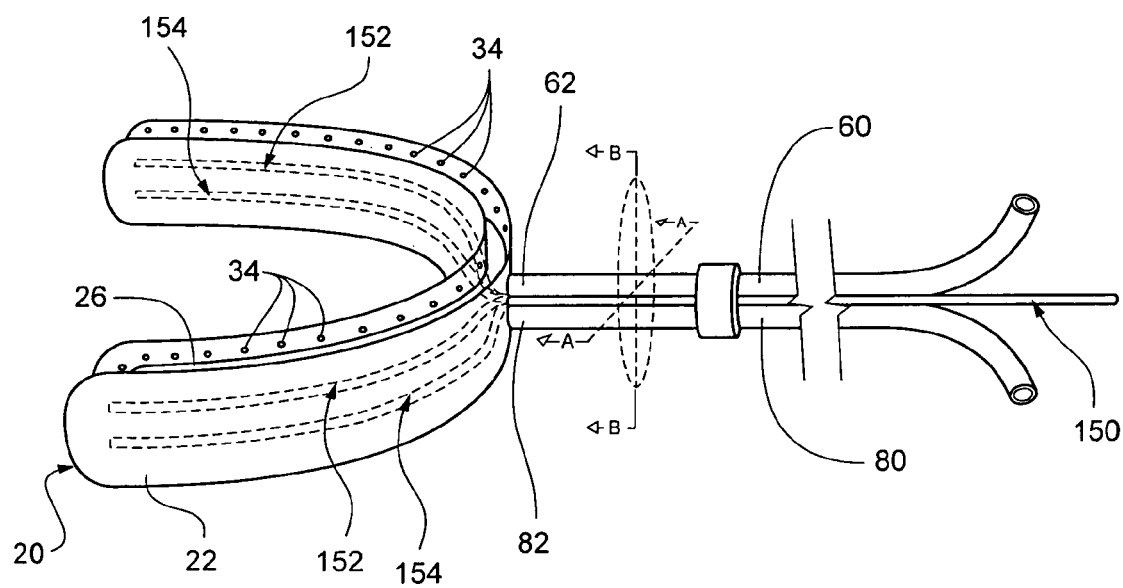
FIG. 2 is a perspective view of a mouth tray of an oral hygiene device according to a preferred embodiment of the present invention.

In describing the preferred and selected alternate embodiments of the present invention, as illustrated in FIGS. 1–5, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIGS. 1–4, the present invention in a preferred embodiment is an oral hygiene device 10 and method of use therefor, comprising, in general, mouth tray 20, dispersion tube 60, collection tube 80, pump unit 120, and light assembly 150.

Figure 4:
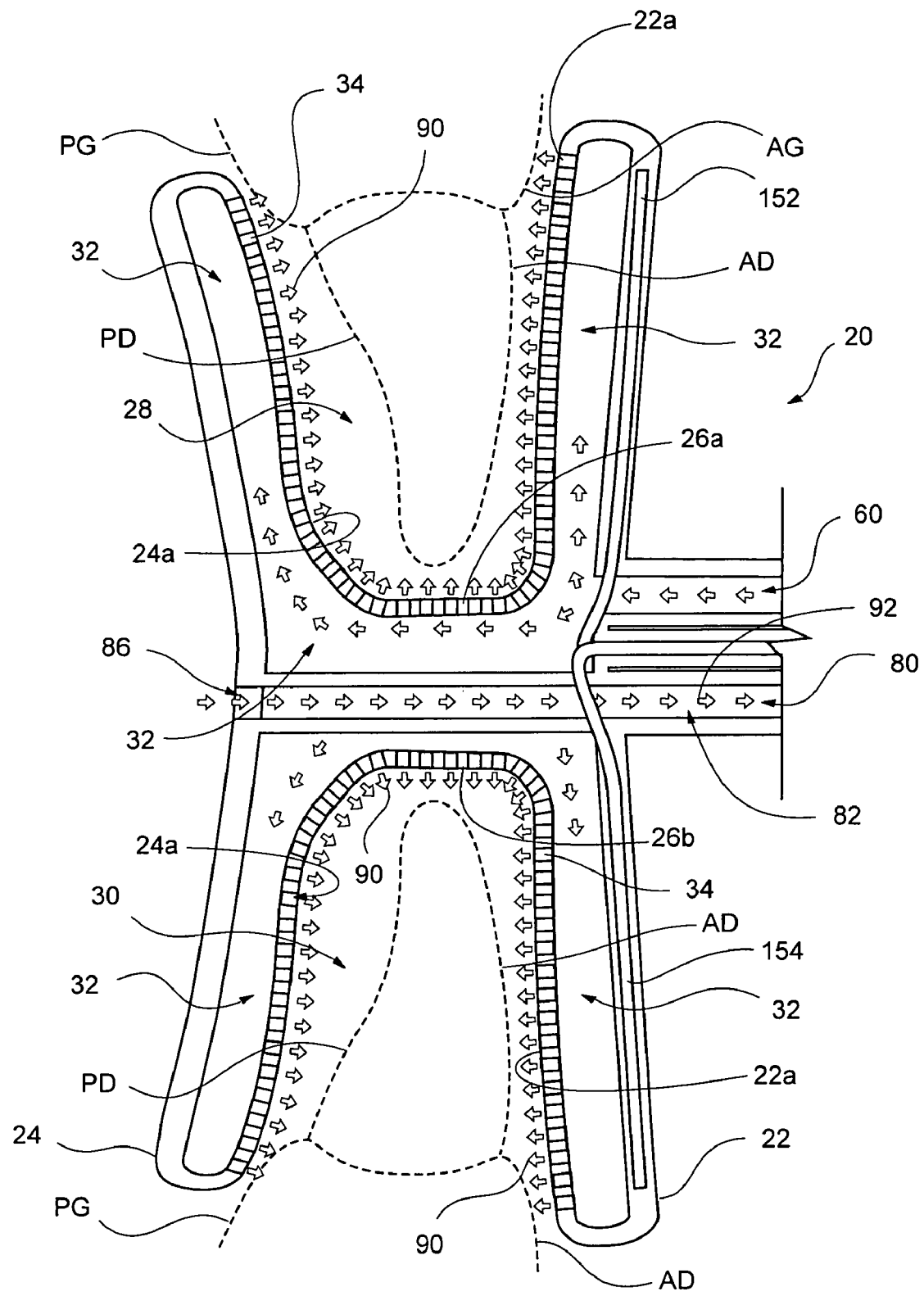
FIG. 4 is a cross-sectional view of a mouth tray of FIG. 2, along section lines B—B; and, FIG. 5 is a cross-sectional view of a mouth tray of FIG. 2, along section lines A—A, according to an alternate embodiment of the present invention.

Mouth tray 20 is preferably substantially U-shaped, and configured or dimensioned to be received within a human mouth. Specifically, mouth tray 20 preferably comprises anterior wall 22, posterior wall 24, and bridge 26 integrally formed therewith and therebetween. Preferably, anterior wall 22, posterior wall 24, and bridge 26 collectively define upper and lower dental seating channels 28 and 30, respectively, for receiving and accommodating the upper and lower rows of teeth, respectively, of the user's mouth. As best illustrated in FIG. 4, anterior wall 22 and posterior wall 24 are preferably dimensioned such that inner surfaces 22a and 24a, respectively thereof, substantially overlap the user's anterior and posterior gum surfaces AG and PG, respectively, thereby ensuring cleansing thereof, as well as the anterior and posterior dental surfaces AD and PD, respectively, and deep-gum and/or deep inter-dental crevices, as more fully described below.

Mouth tray 20 is preferably formed from a clear, semi-flexible material, such as, for exemplary purposes only, silicone; although other suitable, equally effective materials could be utilized. Mouth tray 20 is preferably suitably sized and dimensioned so as to enable a user to effortlessly close his/her mouth and lips therearound, thereby preventing spillage of cleaning solution from the user's mouth during implementation of present cleansing process. Accordingly, it should be recognized that mouth tray 20 may be manufactured to any size for convenient and effective reception of same within a particular user's mouth, wherein such sizes may include, without limitation, extra small, small, medium, large, and extra large. It is further contemplated that mouth tray 20 could be formed from a deformable material so as to allow a user to bite-down thereupon, and thus facilitate temporary conformation of same to the user's particular dental and/or jaw structure. It is still further contemplated that mouth tray 20 could be customized and formed for accurate conformation of same to the user's particular dental and/or jaw structure.

Preferably formed throughout anterior wall 22, posterior wall 24, and bridge 26 of mouth tray 20 in general, is inner space or common manifold 32. Preferably formed through inner surfaces 22a and 24a of anterior wall 22 and posterior wall 24, respectively, and through upper and lower surface 26a and 26b, respectively of bridge 26, is a plurality of throughholes, ports, or orifices 34, wherein orifices 34 are preferably in fluid communication with manifold 32 of mouth tray 20.

Preferably integrally formed with mouth tray 20 and disposed in fluid communication with manifold 32 is first end 62 of dispersion tube 60, preferably extending substantially centrally from outer surface 22b of anterior wall 22. Additionally, preferably penetrably extending substantially centrally through outer surface 22b of anterior wall 22, through bridge 26, and exiting through outer surface 24b of posterior wall 24 of mouth tray 20 is first end 82 of collection tube 80, preferably ending in collection orifice or exposed aperture 86, wherein first end 82 of collection tube 80 preferably extends through mouth tray 20 in such a fashion so as to not interrupt the flow and dispersion of cleansing solution therepast, thereround, through manifold 32 and out through orifices 34, as more fully described below. It is contemplated in an alternate embodiment that first end 62 of dispersion tube 60, and first end 82 of collection tube 80 could be removably secured to mouth tray 20, thereby facilitating the removal of mouth tray 20 therefrom for separate cleansing, rinsing and/or disinfection of same, or selective replacement of same with disposable/other mouth trays 20, following implementation of the present teeth and gum cleansing process.

Preferably, second end 64 of dispersion tube 60 branches into first limb 64a and second limb 64b, wherein first limb 64a is preferably in fluid communication with first dispersion pump 122 of pump unit 120, and wherein second limb 64b is preferably in fluid communication with second dispersion pump 124 of pump unit 120. First dispersion pump 122 is preferably in fluid communication with dentition solution reservoir 126, wherein second dispersion pump 124 is preferably in fluid communication with gingival solution reservoir 128. Preferably, first limb 64a and second limb 64b comprise internally disposed check flow valves 64c and 64d, respectively, for ensuring one-way flow and preventing backflow of cleaning solution conveyed therethrough, as more fully described below.

Similarly, second end 84 of collection tube 80 is preferably in fluid communication with collection pump 130 of pump unit 120, wherein collection pump 130 is preferably in fluid communication with collection reservoir 132. Preferably, second end 84 of collection tube 80 comprises internally disposed check flow valve 84a for ensuring one-way flow and preventing backflow of dirty cleaning solution conveyed therethrough, as more fully described below.

Preferably, pumps 122, 124 and 130 are in removable sealable communication with respective reservoirs 126, 128 and 132 via suitable seal-creating pump valves 122a, 124a and 130a, respectively, thereby permitting the selective removal, cleaning and sealed replacement of respective reservoirs 126, 128 and 132 therewith, for purposes more fully described below. Pumps 122, 124 and 130, and respective reservoirs 126, 128 and 132, are preferably retained within general housing 121 of pump unit 120, wherein activation switch 134, preferably disposed on exterior surface 121a of housing 121 and coupled to pumps 122, 124 and 130, preferably provides the requisite powered control of oral hygiene device 10 in general, as more fully described below. Housing 121 preferably receives lid 123 for covering and shielding reservoirs 126, 128 and 132 of pump unit 120 from foreign debris or the like. Additionally, engaging lid 123 with housing 121 further preferably results in lid 123 contacting and depressing safety switch 125 located on inner surface 121b of housing 121 and disposed in electrical communication with activation switch 134, thereby permitting powered operation of device 10, wherein the non-contact or non-depression of safety button 125 will result in the inoperability of device 10.

First dispersion pump 122 and second dispersion pump 124 are preferably adapted to pump and convey dentition cleansing solution and gingival cleansing solution from respective dentition solution reservoir 126 and gingival solution reservoir 128 through dispersion tube 60 for subsequent dispersion of same through manifold 32 of mouth tray 20, through the plurality of orifices 34 formed throughout mouth tray 20, and thereafter, over the user's teeth and gums, thereby cleansing same.

Specifically, dentition solution reservoir 126 preferably receives a dentition cleansing solution comprising a suitable scrubbing bubble solution that enables the micro-chemical and micro-mechanical scrubbing, loosening and removal of bacterial plaque, tarter and/or food particulate from anterior and posterior gum surfaces AG and PG, respectively, anterior and posterior dental surfaces AD and PD, and deep-gum and/or deep inter-dental crevices. Preferably, gingival solution reservoir 128 preferably receives a gingival cleansing solution comprising ingredients commonly found in conventional mouthwashes, such as, for exemplary purposes only, LISTERINE, CEPACOL, SCOPE, and the like.

Figure 3:
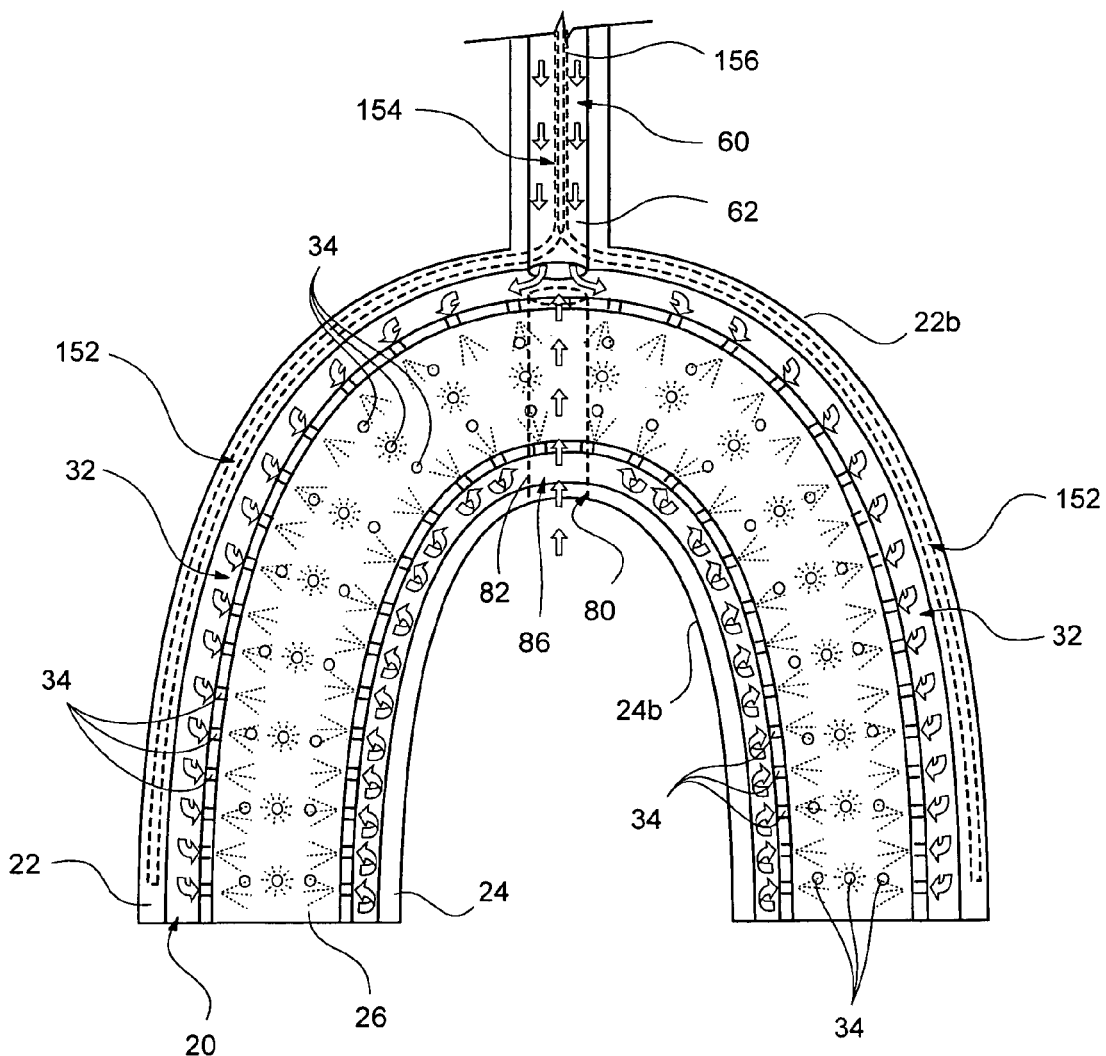
FIG. 3 is a cross-sectional view of a mouth tray of FIG. 2, along section lines A—A.

Accordingly, and as best illustrated in FIGS. 3–4, upon actuation of first dispersion pump 122 via activation switch 134, dentition cleansing solution is preferably pumped, in a forceful and pulsating manner, from dentition solution reservoir 126 through first limb 64a of dispersion tube 60, through check flow valve 64c of first limb 64a, through the length of dispersion tube 60, through manifold 32 of mouth tray 20, and thereafter, through the plurality of orifices 34 of mouth tray 20 for the cleansing, multi-directional, jet-like multi-stream dispersion of same over the user's teeth and gums, as described above, and as illustrated via plurality of directional arrows 90. Preferably, each pulsating delivery of dentition cleansing solution by pump 122 is preferably followed by a brief interruption of delivery of cleansing solution, thereby affording the dentition cleansing solution an opportunity to penetrate teeth and gum-laden bacterial plaque, tartar and food particles, for the micro-chemical and micro-mechanical scrubbing, loosening and removal of same. It is contemplated that device 10 could incorporate programming and timing functions so as to enable a user to selectively adjust the length or duration of pulsating delivery of dentition cleansing solution and/or the periods of cessation of same, thereby enabling within limits of clinical efficacy a user to customize his/her cleansing regimen.

Preferably following cleansing of the teeth and gum structures via dentition cleansing solution as described above, or, alternatively, during the dentition cleansing process, dirty dentition cleansing solution, along with the removed bacterial plaque, tarter and/or food particulate, may be evacuated or suctioned from the user's mouth via activation of collection pump 130 by activation switch 134. Specifically, upon activating collection pump 130, dirty dentition cleansing solution is preferably drawn or suctioned through exposed aperture 86 of first end 84 of collection tube 80 (i.e., disposed on and through outer surface 24b of posterior wall 24 of mouth tray 20 as described above). AS illustrated via directional arrows 92, the dirty dentition cleansing solution is preferably drawn through the length of collection tube 80, through check flow valve 84a of collection tube 80, through collection pump 130, and into collection reservoir 132 of pump unit 120. Alternatively, it is contemplated that dentition solution reservoir 126, gingival solution reservoir 128, and in particular, collection reservoir 132, could each comprise a manual or automated drainage or plumbing system to enable the flushing of cleaning solution and/or dirty cleaning solution, respectively, therefrom, wherein suitable sanitizing solutions or disinfectants may be subsequently introduced therein and, thereafter, flushed or drained therefrom, thereby supporting a larger clinical application of the present invention.

Thereafter, upon actuation of second dispersion pump 124 via activation switch 134, gingival cleansing solution is preferably pumped from gingival solution reservoir 128 through second limb 64b of dispersion tube 60, through check flow valve 64d of second limb 64b, through the length of dispersion tube 60, through manifold 32 of mouth tray 20, and thereafter, through the plurality of orifices 34 of mouth tray 20 for the cleansing, multi-directional, jet-like multi-stream dispersion of same over the user's teeth and gums, as described above, and as illustrated via plurality of directional arrows 90. Preferably, gingival cleansing solution further facilities the removal of any vestigial bacterial plaque, tartar and/or food particles, wherein collection pump 130 is preferably actuated following the gingival cleansing process for removal of the dirty gingival cleansing solution, along with any vestigial plaque, tartar and/or food particulate, as described above.

Preferably, dispersion reservoirs 126 and 128, and/or collection reservoir 132 of pump unit 120 may each be selectively removed from resealable communication with respective seal-creating pump valves 122a, 124a and 130a, for the cleansing, rinsing and/or disinfection of same.

Preferably, following the above-described cleansing process, a user may selectively opt to conduct a self-administered light-activated beaching process as provided via oral hygiene device 10 and associated light assembly 150. Specifically, light assembly 150 preferably includes side-emitting fiber optic light lines 152 and 154, preferably integrally formed with and embedded along outer surface 22b of anterior wall 22 of mouth tray 20 in such an arrangement or configuration so as to concentrate the light conveyed therethrough over the front surfaces (i.e., anterior dental surfaces AD) of the upper and lower teeth, as best illustrated in FIG. 4. Fiber optic light lines 152 and 154 preferably extend from mouth tray 20 to pump unit 120, and are preferably encased within protective exterior sheath 156. Moreover, fiber optic light lines 152 and 154 are preferably in communication with a suitable powered lamp or illuminator 158 contained within pump unit 120 and actuated via activation switch 134.

Accordingly, a light-activated bleaching compound may be directly applied to anterior dental surface AD of a user's teeth, to upper and lower dental seating channels 28 and 30 of mouth tray 20, or delivered via pump unit 120 through dispersion tube 80 for subsequent dispersion of same through orifices 34 and over the user's teeth. Illumination of fiber optic light lines 152 and 154 via activation switch 134 and illuminator 158 preferably enables the illumination, and thus activation, of the bleaching compound over the teeth, thereby expediting and/or enhancing the bleaching or whitening process thereof. The present invention contemplates that a suitable light or photon-activated bleaching compound may comprise a 20% hydrogen peroxide (i.e., a bleaching agent) and 1.1% neutral sodium fluoride (i.e., a desensitizing agent) composition, preferably carried within a suitable gel agent to facilitate effective coverage and temporary adherence of same over the anterior dental surface AD of the user's teeth. However, it should be recognized that any other suitable light/photon-activated bleaching compound may be utilized to implement the bleaching process of the present invention. It is further contemplated that fiber optic light lines 152 and 154 may be illuminated during the cleansing process of the teeth, wherein a suitable bleaching compound could be intermixed with, or applied in conjunction with, the dentition and/or gingival cleansing solution over the teeth and gums, for activation of same via fiber optic light lines 152 and 154. It is still further contemplated that fiber optic light lines 152 and/or 154, and/or selected portions or sections thereof, may be selectively activated or illuminated to permit the selective bleaching of the lower teeth, upper teeth, and/or selected regions of the user's dental structure. It is also contemplated that similar light emitters, carriers, reflectors and/or sources may be integrally formed with and embedded along outer surface 24b of posterior wall 24 to facilitate light-activated bleaching processes of the posterior dental surfaces PD of the upper and lower rows of teeth.

Although side-emitting fiber optic light lines 152 and 154 are preferred, it should be recognized that other suitable light emitters, carriers, reflectors and/or sources could be utilized to effectuate the present light-activated bleaching process, wherein such alternate light emitters, carriers, reflectors and/or sources may include, without limitation, flat woven fiber optic panels or strips, side-emitting fiber optic light lines, lasers, blue light, light-emitting diodes, edge-emitting diodes, surface-emitting diodes, and/or the like.

Figure 5:
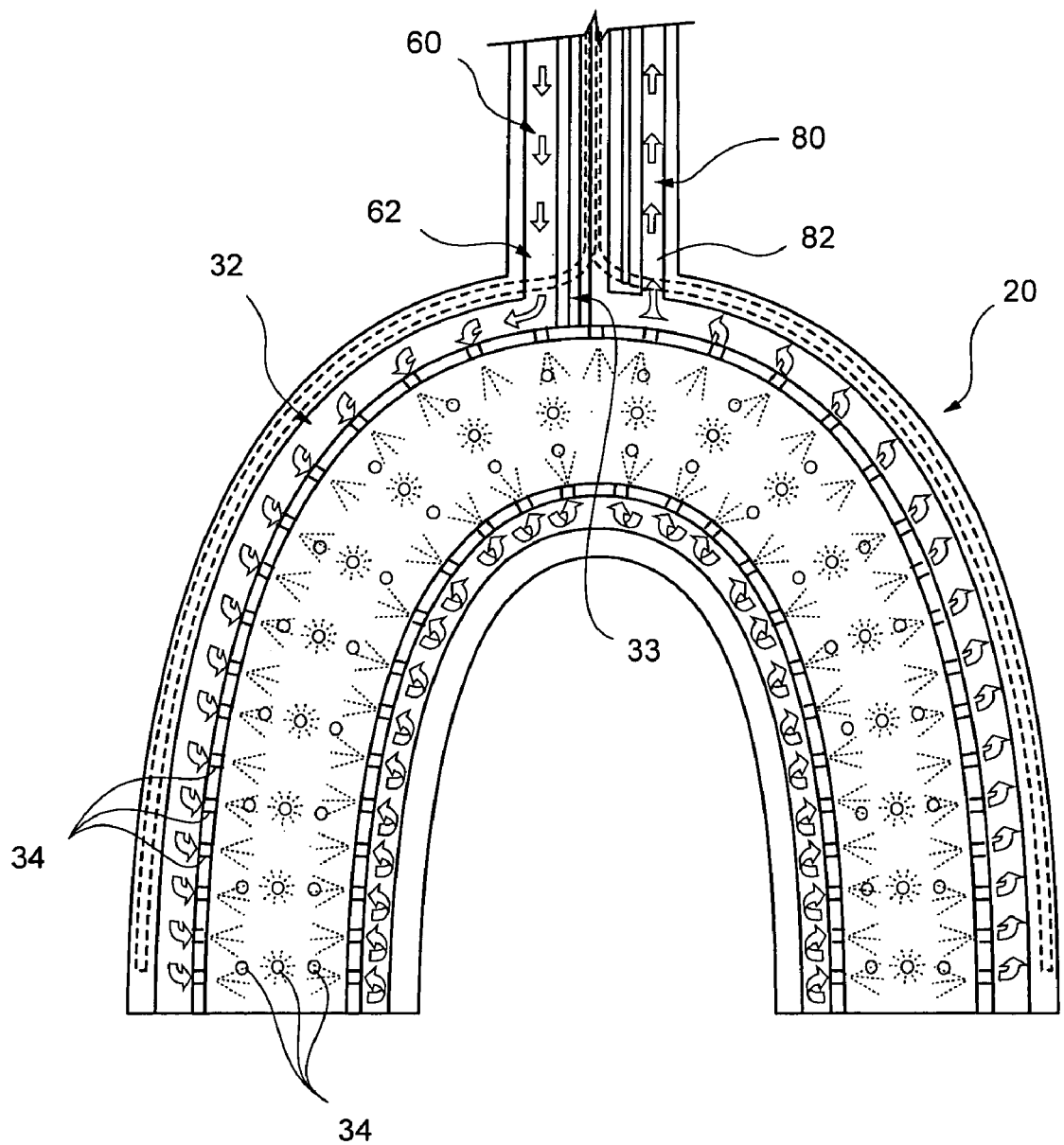

Referring now more specifically to FIG. 5, illustrated therein is an alternate embodiment of device 10, wherein the alternate embodiment of FIG. 5 is substantially equivalent in form and function to that of the preferred embodiment detailed and illustrated in FIGS. 1–4 except as hereinafter specifically referenced. Specifically, the embodiment of FIG. 5 integrally forms or disposes first end 82 of collection tube 80 in fluid communication with manifold 32 of mouth tray 20, wherein barrier or separating wall 33 formed within manifold 32 divides first end 82 of collection tube 80 from first end 62 of dispersion tube 60. As such, cleaning solution pumped and conveyed through dispersion tube 60 is channeled unidirectionally through manifold 32 as a result of separating wall 33. Thereafter, collection pump 130 may be activated to enable the evacuation or suctioning of dirty dentition cleaning solution from the user's mouth and mouth tray through collection tube 80, wherein dirty dentition cleaning solution, along with removed bacterial plaque, tarter and/or food particulate, is drawn back through the plurality of orifices 34 of mouth tray 20 and into collection reservoir 132 contained within pump unit 120.

It should be recognized that the steps of the present cleansing and bleaching processes, whether of the preferred and/or alternate embodiments of the present invention, may be performed or implemented in any selected order to fashion or tailor a particular dental hygiene program or regimen to meet the specific needs and demands of a user.

It should be further recognized that the present invention advantageously provides an automated oral hygiene device incorporating, in combination, a teeth and gum cleansing system, and a teeth bleaching system, wherein the present invention may be in utilized in conjunction with, or in lieu of, conventional brushing, flossing and/or bleaching practices. It should still further be recognized that the present invention may be utilized by those individuals suffering from physical incapacities that may hinder the practice of regular oral hygiene, wherein such individuals may include the elderly, arthritis sufferers, paraplegics, quadriplegics, bed-ridden individuals, hospitalized individuals, and the like.

It is contemplated in an alternate embodiment that mouth tray 20 could comprises a plurality of orifices formed through the entire surface thereof, thereby permitting the oral cleansing of inner cheek tissues, the tongue and inner lip tissues, thus promoting a "gargling and/or drowning effect."

It is contemplated in another alternate embodiment that collection tube 80 could be a non-pump powered evacuation or drainage tube.

It is contemplated in still another alternate embodiment that the present invention could incorporate a flow control for selectively adjusting the amount of cleaning fluid delivered through dispersion tube 60 and mouth tray 20.

It is contemplated in yet another alternate embodiment that the present invention could incorporate a lip closure hub formed proximal first end 82 of collection tube 80 and first end 62 of dispersion tube 60, thereby facilitating the comfortable closure or wrapping of a user's lips therearound when mouth tray 20 is disposed within the user's mouth, and thus, further preventing spillage of cleaning fluid therefrom.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. An oral hygiene device, comprising:
    a mouth tray comprising means for directing a cleaning solution over at least a portion of a user's dental and gum structures; and,
    a light carrier in communication with at least a portion of said mouth tray, said light carrier adapted to facilitate light-activated bleaching processes.

2. The oral hygiene device of claim 1, wherein said mouth tray comprises an inner manifold formed therethrough.

3. The oral hygiene device of claim 2, wherein said means for directing further comprises a plurality of orifices disposed over at least a portion thereof, said plurality of orifices in fluid communication with said manifold.

4. The oral hygiene device of claim 3, wherein a dispersion pump delivers the cleaning solution from a dispersion reservoir through a dispersion tube in fluid communication with said manifold of said mouth tray, and wherein the cleaning solution enters said manifold for subsequent expulsion of the cleaning solution through said plurality of orifices.

5. The oral hygiene device of claim 4, wherein said dispersion pump delivers the cleaning solution through said dispersion tube in a pulsating manner for pulsating dispersions of same through said manifold, and thereafter, through said plurality of orifices of said mouth tray for the forceful dispersion of the cleansing solution over the user's dental and gum structures, thereby affording the micro-chemical or micro-mechanical scrubbing, loosening and removal of bacterial plaque, tartar and food particulate from same.

6. The oral hygiene device of claim 5, wherein the pulsating delivery and dispersion of the cleaning solution by said dispersion pump is followed by a period of interruption of delivery of the cleaning solution by said dispersion pump, thereby affording the dispersed cleaning solution an opportunity to contact the user's dental and gum structures for the micro-chemical or micro-mechanical scrubbing, loosening and removal of bacterial plaque, tartar and food particulate from same.

7. The oral hygiene device of claim 6, wherein said mouth tray further comprises a collection tube carried thereby.

8. The oral hygiene device of claim 7, wherein said collection tube is in communication with a collection pump, said collection tube and said collection pump facilitating the suctioning and conveyance of dirty cleaning solution from the user's mouth to a collection reservoir or evacuation and drainage means.

9. The oral hygiene device of claim 8, wherein said dispersion reservoir comprises a dentition cleaning solution reservoir and a gingival cleaning solution reservoir for receiving dentition cleaning solution and gingival cleaning solution, respectively, for selective delivery of same through said dispersion tube for application over at least a portion of the user's dental and gum structures.

10. The oral hygiene device of claim 9, wherein said dentition cleaning solution reservoir, said gingival cleaning solution reservoir, and said collection reservoir are removable for the rinsing, cleansing and disinfection of same.

11. The oral hygiene device of claim 1, wherein said light carrier is selected from the group consisting of side-emitting fiber optic light lines, flat woven fiber optic panels, flat woven fiber optic strips, side-emitting fiber optic light lines, lasers, blue light, light-emitting diodes, edge-emitting diodes, surface-emitting diodes, and combinations thereof.

12. The oral hygiene device of claim 11, wherein said light carrier is integrally formed with said mouth tray.

13. The oral hygiene device of claim 12, wherein said light carrier is adapted to activate a light-activated bleaching compound applied to at least a portion of the user's dental structure to facilitate, expedite and enhance the bleaching or whitening thereof.

14. An oral hygiene device, comprising:
    a mouth tray adapted to direct a plurality of forceful, pulsating, multi-directional jet-like streams of a cleaning solution over and between at least a portion of a user's dental and gum structures; and,
    a light carrier in communication with at least a portion of said mouth tray, said light carrier adapted to facilitate light-activated bleaching processes.

15. The oral hygiene device of claim 14, wherein said mouth tray comprises an anterior wall, a posterior wall, and a bridge integrally formed therewith and therebetween.

16. The oral hygiene device of claim 15, wherein said anterior wall, said posterior wall, and said bridge comprise a common manifold formed therethroughout.

17. The oral hygiene device of claim 16, wherein said anterior wall, said posterior wall, and said bridge further comprise a plurality or orifices disposed over at least a portion thereof, said plurality of orifices in fluid communication with said manifold.

18. The oral hygiene device of claim 17, wherein a dispersion pump delivers the cleaning solution from a dispersion reservoir through a dispersion tube in fluid communication with said manifold of said mouth tray, and wherein the cleaning solution enters said manifold for subsequent expulsion of the cleaning solution through said plurality of orifices as a plurality of forceful, pulsating, multi-directional jet-like streams.

19. The oral hygiene device of claim 18, wherein the forceful and pulsating delivery and dispersion of the cleaning solution over and between at least a portion of the user's dental and gum structures is followed by a period of interruption of dispersion of the cleaning solution, thereby affording the dispersed cleaning solution an opportunity to contact the user's dental and gum structures for the micro-chemical or micro-mechanical scrubbing, loosening and removal of bacterial plaque, tartar and food particulate from same.

20. The oral hygiene device of claim 19, wherein said mouth tray further comprises a collection tube carried thereby.

21. The oral hygiene device of claim 20, wherein said collection tube is in fluid communication with said manifold of said mouth tray, and wherein said collection tube, via assistance from a collection pump, facilitates the suctioning and conveyance of dirty cleaning solution from the user's mouth back through said plurality of orifices of said mouth tray, through said collection tube, and into a collection reservoir or evacuation and drainage means.

22. The oral hygiene device of claim 20, wherein said collection tube extends through said anterior wall, through said bridge, and exits through said posterior wall, thereby creating a collection orifice.

23. The oral hygiene device of claim 22, wherein said collection tube is in communication with a collection pump, said collection tube and said collection pump facilitating the suctioning and conveyance of dirty cleaning solution from the user's mouth through said collection orifice, through said collection tube, and into a collection reservoir.

24. The oral hygiene device of claim 14, wherein said light carrier is selected from the group consisting of side-emitting fiber optic light lines, flat woven fiber optic panels, flat woven fiber optic strips, end-emitting fiber optic light lines, lasers, blue light, light-emitting diodes, edge-emitting diodes, surface-emitting diodes, and combinations thereof.

25. The oral hygiene device of claim 24, wherein said light carrier is integrally formed with said anterior wall of said mouth tray.

26. The oral hygiene device of claim 25, wherein said light carrier is adapted to activate a light-activated bleaching compound applied to at least a portion of the user's dental structure to facilitate, expedite and enhance the bleaching or whitening thereof.

* * * * *